United States Patent [19]

Wilson et al.

[11] 4,096,746
[45] Jun. 27, 1978

[54] FLOW CONTROLLER-FLOW SENSOR ASSEMBLY FOR GAS CHROMATOGRAPHS AND THE LIKE

[75] Inventors: Francis P. Wilson, Oxford; John E. Purcell, Riverside, both of Conn.

[73] Assignee: The Perkin-Elmer Corporation, Norwalk, Conn.

[21] Appl. No.: 772,179

[22] Filed: Feb. 25, 1977

[51] Int. Cl.² ........................ G01F 1/34; G01F 25/00
[52] U.S. Cl. ...................... 73/205 R; 73/3; 73/23.1; 137/501
[58] Field of Search ............. 73/23.1, 205 R, 3; 137/501; 138/43, 46

[56] References Cited

U.S. PATENT DOCUMENTS

| | | | |
|---|---|---|---|
| 1,640,842 | 8/1927 | Loomis | 137/501 |
| 1,699,676 | 1/1929 | Rush | 137/501 |
| 2,182,873 | 12/1939 | King | 137/501 |
| 2,711,187 | 6/1955 | Bowditch | 137/501 |
| 2,862,162 | 11/1958 | Baring | 73/205 R |
| 3,078,713 | 2/1963 | Schlieder | 73/205 R |
| 3,792,609 | 2/1974 | Blair et al. | 73/205 R |

Primary Examiner—Richard C. Queisser
Assistant Examiner—Stephen A. Kreitman
Attorney, Agent, or Firm—Sal A. Giarrantana; Francis L. Masselle; Edwin T. Grimes

[57] ABSTRACT

There is disclosed a flow controller-flow sensor combination especially suited for gas chromatograph applications wherein a transducer monitors the pressure at the inlet and outlet of a flow restrictor element in the controller thereby to monitor the differential pressure across the restrictor; the differential pressure being proportional to the gas velocity through the flow restrictor element. In one form of the invention, a second flow restrictor element is provided in one input line to the transducer which preferably is of relatively low impedance in order to delay the buildup of the pressure head of the corresponding input of the transducer sensor, thus to enable the pressure at the outlet of the flow restrictor in the controller to buildup gradually so as not to exceed the maximum differential pressure specifications for said transducer.

6 Claims, 3 Drawing Figures

FLOW CONTROLLER-FLOW SENSOR ASSEMBLY FOR GAS CHROMATOGRAPHS AND THE LIKE

BACKGROUND OF THE INVENTION

This invention relates to flow controllers generally and more particularly to a flow controller which has a flow sensor as an integral part thereof to sense the flow rate through the controller.

Flow controllers are well known in the gas chromatography field (and others) as a means for regulating the flow of carrier gases in the system. They afford a means to maintain a constant flow independent of any pressure variations in the system down stream of the device, such as a dual-column gas chromatograph, which may result from variable impedances such as, for example, temperature programming, line restrictions, or column switching.

Prior art systems have always installed the controller and sensor in different spaced apart locations in the system. Typical prior art sensors, such as the mass flow sensor manufactured by Brooks Instrument Division of Emerson Electric Co., Hatfield, Pennsylvania, were quite expensive in that they included a resistive bridge network, with thermistors positioned in the gas stream, a power supply and other control electronics. This relatively complicated arrangement, due to component tolerances, mismatching, etc., could easily introduce errors into the "detected" flow rate. The result was that oftentimes, the flow controller was made to compensate for these latter changes, altering the flow rate when in fact, the system did not require such a change.

It is therefore an object of this invention to provide a controller-sensor arrangement, which does not adjust the flow rate directly for any errors inherent in the sensor.

It is another object of this invention to provide a simplified sensor arrangement, which measures a pressure differential across the controller, thus providing a means for detecting system leaks as well as a more meaningful flow measurement.

It is still another object of the invention to provide a sensor which provides an electrical output proportional to the pressure differential across the controller and thus to the flow rate therethrough.

It is yet another object of the invention to provide a controller-sensor arrangement which can measure differential pressures in the range of from about 0 to about 15 psi, while monitoring gases maintained at about 100 psi absolute pressure.

It is still another object of this invention to provide an arrangement, which allows the use of low differential pressure transducers in high pressure systems, where the full range of said transducers is employed so as to give more accurate and repeatable flow rate readings.

SUMMARY OF THE INVENTION

Towards the accomplishment of these and other objects and advantages, which will become apparent from the following description and accompanying drawings, there is described a flow controller-flow sensor combination, having particular application in the gas chromatography field. The flow sensor, preferably in the form of a low differential pressure-type transducer, includes a first and second port which are connected to the inlet and outlet, respectively, of a first flow restrictor element positioned in the controller. The transducer is of a type which provides an electrical signal proportional to the differential pressure across its ports.

In a preferred embodiment of the invention, a second flow restrictor element is connected in the inlet line leading to the first port of the transducer. The second flow restrictor element has similar flow rate characteristics, under the particular system constraints, as the first restrictor in the controller. This second restrictor delays the pressure buildup at the first port of the transducer so as to enable the pressure at the second port (which is connected directly to the outlet of the first restrictor) to build to a level sufficient to ensure that the pressure differential across the two ports of the transducer never exceeds the maximum allowable. Thus, a transducer having a maximum range on the order of the pressure differential to be experienced, can be employed, providing relatively high accuracy readings. By first calibrating the flow through the controller as a function of pressure across the first restrictor and then obtaining an electrical signal proportional to corresponding pressures, a matched linearization curve can be obtained, which provides a future reference to enable ready determination of the flow rate through the controller for any given electrical output of the transducer.

BRIEF DESCRIPTION OF THE DRAWINGS

What follows is a description of preferred embodiments of the present invention which is to be read in conjunction with the accompanying drawings for a better understanding. In the drawings.

DESCRIPTION OF THE PREFERRED EMBODIMENTS

Figure 1:
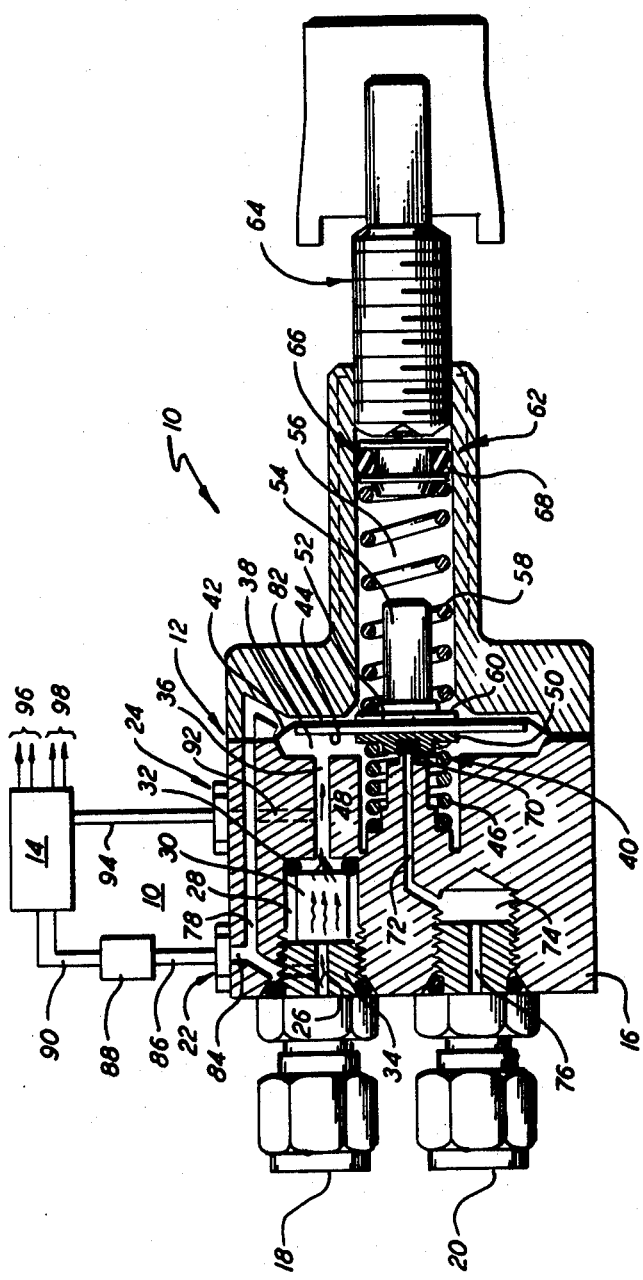
FIG. 1 is in part an elevational view and in part a schematic block diagram of the present invention.

Referring to FIG. 1, there is shown, partially in section and partially in block diagram form, the assembly which effects the purposes of this invention. The flow controller-flow sensor assembly, 10, includes a flow controller 12 which is interconnected to a transducer 14.

The flow controller 12 includes a main housing portion 16 which is, typically, fabricated from aluminum or stainless steel. Positioned at one end of the housing are inlet and outlet ports 18 and 20, respectively. Located on an adjoining side are specially provided taps or outlets, 22 and 24. These will be described more fully hereinafter.

Without the modifications to be discussed hereinafter, the basic flow controller depicted in FIG. 1 is similar in construction to Porter Instrument Co., Inc. model number VCD 1000. It includes a cylindrical inlet channel 26 which connects the inlet port 18 to a cavity 28. Positioned in the cavity 28 is a flow restrictor element 30, which is a sintered metal element of controlled porosity to provide a certain flow rate per minute, which is a function of its porosity, the differential pressure across it, the density of the carrier gas employed in the system and other known factors. Also positioned in the cavity 28 is an O-ring 32 made of rubber or other suitable material which butts up against the outer perimeter of the flow restrictor element 30 to eliminate any leakage paths for the gas flow (shown by the arrows). The inlet assembly 18 includes a threaded stem portion 34, which includes the cylindrical channel 26, said stem portion being removable from the housing in order to provide access to the flow restrictor element for reasons soon to be discussed.

The carrier gas once it exits from the flow restrictor element 30 is directed by a connection channel 36 into a pancake-shaped chamber 38. Positioned in the latter is a shutoff and internal control valve assembly, indicated at 40. This assembly is employed to vary the pressure across the flow element, thereby to regulate the flow rate through the controller. Valve assembly 40 includes a diaphragm, 42, made out of a suitable material such as neoprene, for example, and which has centrally positioned on one side thereof a backing plate 44. On the same side of the diaphragm as the backing plate 44, is a spring member 46 which sits on a shoulder 48 and is biased against a seat 50 mounted on the backing plate 44. The spring is centrally disposed with respect to the backing plate 44 to exert a balanced force thereon. Positioned on the other side of the diaphragm is a second backing plate 52, which includes a stem portion 54 centrally disposed thereon and which extends axially into a cavity 56. Extending the length of the cavity 56 is a second spring member, 58, which is seated on a shoulder 60 on the backing plate 52 and which is biased against a valve assembly 62. The latter is connected to a threaded stem portion 64 for controlling the axial movement of the valve assembly 62 and thus, in turn, the spring pressure exerted by the spring 58 upon the diaphragm 42. The valve assembly includes a sealing mechanism 66 including an O-ring member 68, which seals the cavity 56 to eliminate leakage of the carrier gas past the threaded stem member 64.

The internal control valve assembly 40 also includes a sealing gasket 70, which moves with the diaphragm 42 to vary the carrier gas flow into the inlet end of a channel 72, depending on the relative magnitude of the spring forces being exerted on the diaphragm by spring members 46 and 58. The relative spring force exerted on the diaphragm is varied by rotating the stem member 64 into or out of the cavity 56. This provides an infinite adjustment of the gas flow, allowing for a highly accurate flow controller. The gas at the controlled rate enters the channel 72 and is directed down into cavity 74 and exit channel 76 and thence to the outlet valve 20.

A bypass duct 78 is connected at one end to the inlet channel 26 and at the other end to the chamber 82, which communicates with the cavity 56 on the corresponding side of the diaphragm. This bypass duct equalizes the pressure on opposite sides of the diaphragm, making it impossible for the diaphragm in the shutoff condition to be pressurized on one side only.

The flow controller just described is modified for the purposes of this invention, as follows. The housing 16 is drilled through to provide a connection channel 84 between the duct 78 and one of the exterior faces at, particularly, the tap 22. Appropriately sized metal tubing 86 connects this point through a suitable coupling to a second flow restrictor element 88. This element, preferably, is a sintered metal element of controlled porosity to provide a time delay for the gas passing through the tubing 86. The delay is comparable to the one experienced by the gas as it flows through the flow restrictor element 30. The delay provided for by element 88 insures that the pressure differential across the sensor 14 will not exceed its specifications. The delay for a typical application is of the order of from about 15 to about 20 seconds. The flow restrictor element 88 is connected to a first input port of the transducer 14 by tubing 90.

A second channel 92 is drilled in the housing 16 and connected to the channel 36, which is down stream from the flow restrictor element 30. Channel 92 is connected to the second input port of the transducer 14 through an appropriate coupling 24 and tubing 94.

Any suitable general purpose pressure transducer may be employed such as, for example, type AB-15 as manufactured by the Tyco Instrument Division of Lexington, Massachusetts.

Such transducers feature a wide range of differential pressures with accuracies including non-linearities, hysteresis effects and repeatability, on the order of 0.5–1.0%. The transducer is electrically powered at leads 96 and provides an electrical signal output at leads 98, which is proportional to the differential pressure monitored by the transducer in tubing 90 and 94.

As pointed out hereinbefore, the flow restriction element 88 introduces an appropriate time delay so that the transducer 14 does not "see" a differential pressure greater than the specified maximum for the unit. This enables the transducer to withstand high absolute pressures at each of its ports while only experiencing a relatively small differential pressure, thereby allowing it to perform within its specified accuracy.

Figure 2:
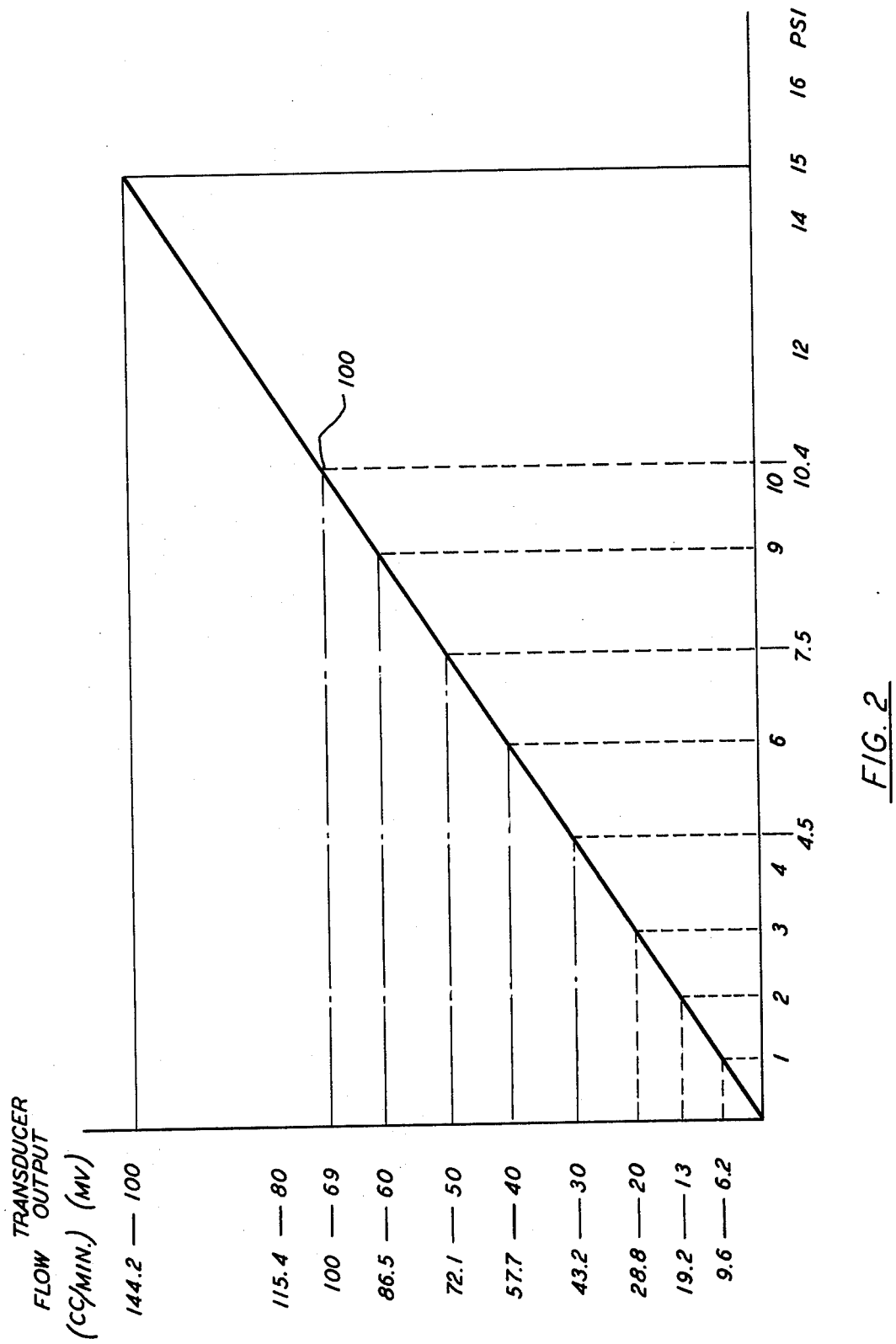
FIG. 2 is a graph depicting matched linearization curves for flow and transducer output versus pressure.

Referring now to FIG. 2, the method for setting up the combined assembly so as to provide a linearization curve showing flow in cubic centimeters or milliliters per minute in terms of millivolts of output at leads 98 of the transducer vs. the differential pressure across the flow controller will be described. A flow restriction element 30 is selected, which has a specified flow rate per differential pressure characteristic appropriate for the particular application. For example, one such element might be purchased as an off-the-shelf item having a flow rate of 120 cc/min. at a differential pressure of 10.4 psi. As is well known in the art, the flow rate of a flow restriction element can be adjusted below the nominal flow rate by compacting the porous material, e.g., by striking it sharply with a suitable tool. For example, the flow rate for a 120 cc/mm. unit at 10.4 psi can be adjusted downward to 100 cc/min. at 10.4 psi differential pressure. The element once adjusted is then inserted into cavity 28 of the flow controller. The flow rate of 100 cc/min. at 10.4 psi, point 100 on the linearization curve of FIG. 2, would be set for a particular axial position of stem 64 or opening of valve assembly 40.

By rotating the stem 64 of the flow controller, the flow therethrough can be adjusted from shutoff to 100%. By tabulating the flow through the controller, i.e., cc/min. for various settings of the stem 64 (and thus the pressure differential across the flow restriction element 30), the remainder of the curve of FIG. 2 can be constructed. By thereafter connecting the pressure transducer according to the diagram of FIG. 1, and varying the stem adjustment in the same manner as was done when setting the flow rate vs. pressure curve, the corresponding MVDC output from the pressure transducer at leads 98 with respect to the stem setting or the pressure can be established.

Typically, transducer 14 will have a zero to 100 millivolt D.C. output at leads 98 for the full range of differential pressure expected to be experienced for a particular unit. In the case where the transducer is designed to handle a 0–15 psi differential, where the pressure across the element 30 at a flow rate of 11 cc/min. is on the order of 10.4 psi, the D.C. output from the transducer 14 would be approximately two-thirds of its maximum output or, as actual measurements have shown, approximately 69 MVDC.

The graph of FIG. 2 reflects matched linearization curves for a gas chromatography system employing helium as the carrier gas at an absolute supply pressure at the input valve, 18, of 75 psi.

Different linearization curves are established for the flow controller-flow sensor based on the particular type of gas employed, as well as for the particular supply pressure employed, i.e., the absolute pressure at the intake valve 18, which variables exist for differing applications of the gas chromatograph.

Figure 3:
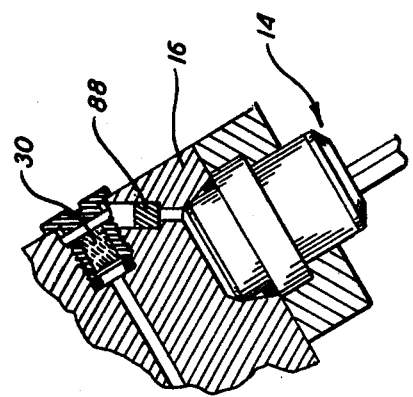
FIG. 3 is a sectional view of a typical flow controller adapted to include a time delay element and a transducer to effect the purposes of the invention.

Other modifications to the design described above will be apparent to those skilled in the art. In particular, whereas the pressure transducer 14 is shown in FIG. 1 to be separate and apart from the flow controller, 12, in fact, the size of the components such as the flow restrictor element 88 and the transducer 14 can be such that appropriate openings can be drilled in the housing 16 of the flow controller such as Potter Industry's VCD 1000 type, which will enable the actual positioning of those elements in the housing itself without the need of the connecting tubing 86, 90 and 94. Such an arrangement is shown in the sectional view of FIG. 3.

The MVDC output appearing on lead 98, reflecting the actual flow through the instrument, can be connected to a suitable display, which will give an immediate indication (by checking the linearization chart for the particular device) of the actual flow rate through the chromatograph.

Further, the electrical signal output of the transducer can be fed to a comparator network (not shown) which has its other input controlled by the axial position of stem 64. The latter is set at a predetermined position corresponding to a desired flow rate. When the fluid in the system reaches the selected flow rate (as sensed by the transducer) the electrical signal reflects this and the comparator is operated to give an indication such as, for example, lighting a display light.

Unlike typical flow sensors which operate independently of the actual controlling device, the sensor of the present invention is connected integrally with the controller and as such will sense any pressure and corresponding flow changes that occur in the system. As a result, not only does the device provide a more meaningful flow measurement, but, in addition, indirectly serves as a leak detector.

With the combination described above, a flow sensor of the low differential pressure transducer type can be employed in high absolute pressure systems. Thus, the full range of the transducer is utilized to improve the accuracy and repeatability of the readings obtained.

The preferred embodiments described above are not to be construed as limiting the breadth of the invention, the scope of which is properly defined by the appended claims.

What is claimed is:

1. A flow controller-flow sensor assembly for regulating the flow of fluid through a system, comprising, in combination:
   inlet channel means;
   first flow restrictor means having an inlet and outlet for passing said fluids, said flow restrictor means having its inlet positioned in fluid flow communication with said inlet channel means, said first flow restrictor means being responsive to the difference in pressure between its inlet and outlet to thereby control the flow rate through said system;
   means disposed on the outlet side of said flow restrictor means for varying the pressure between the inlet and outlet of said flow restrictor means so as to vary said flow rate;
   outlet channel means in fluid flow communication with the outlet of said restrictor means for returning the fluid within the controller to the system;
   transducer means having a first and a second port;
   means for connecting said first port to the inlet of said flow restrictor means in fluid flow communication;
   said transducer means including means for generating an electrical signal proportional to the pressure difference between said first and second ports;
   said means for connecting said first port to the inlet of said flow restrictor means including a second flow restrictor means, said second flow restrictor means having substantially the same flow rate characteristics as the first flow restrictor means so that the time it takes for said first port to sense the pressure at the inlet of said first flow restrictor means is substantially equal to the time it takes for the pressure at the outlet of said first flow restrictor means to build up to its anticipated value based on the setting of said means for varying the pressure between the inlet and outlet of said first flow restrictor means.

2. The apparatus of claim 1 wherein the transducer means has a full scale pressure range substantially equal to the maximum differential pressure to be experienced by said first flow restrictor means.

3. The apparatus of claim 1 wherein said first flow restrictor means is made of sintered metal of controlled porosity.

4. The apparatus of claim 3 wherein said second flow restrictor means is made of sintered metal of controlled porosity.

5. The apparatus of claim 3 wherein the flow rate versus differential pressure characteristic of said first flow restrictor means is adjustable.

6. A method for calibrating a flow controller-flow sensor assembly for regulating the flow of fluid through a system having inlet channel means; first flow restrictor means having an inlet and outlet for passing said fluids, said flow restrictor means having its inlet positioned in fluid flow communication with said inlet channel means, said first flow restrictor means being responsive to the difference in pressure between its inlet and outlet to thereby control the flow rate through said system; means disposed on the outlet side of said flow restrictor means for varying the pressure between the inlet and outlet of said flow restrictor means so as to vary said flow rate; outlet channel means in fluid flow communication with the outlet of said restrictor means for returning the fluid within the controller to the system; transducer means having a first and a second port; means including a second flow-restrictor means for connecting said first port to the inlet of said flow restrictor means in fluid flow communication; said transducer means including means for generating an electrical signal porportional to the pressure difference between said first and second ports; said method comprising the steps of:
   (a) obtaining a plurality of corresponding flow rates through said controller for a predetermined plurality of differential pressures across said first flow restrictor means;

(b) tabulating said flow rates and their corresponding differential pressures;
(c) obtaining a plurality of electrical signals from said transducer means proportional to each of said corresponding differential pressures; and
(d) tabulating said electrical signals with the tabulation of step (b) in a form which allows for ready determination of the flow rate through said controller based on a particular electrical signal produced by said transducer means.

* * * * *